(12) United States Patent
Harttig

(10) Patent No.: US 11,627,897 B2
(45) Date of Patent: Apr. 18, 2023

(54) MEDICAL DEVICE AND PROCESS FOR MANUFACTURING

(71) Applicant: ROCHE DIABETES CARE, INC., Indianapolis, IN (US)

(72) Inventor: Herbert Harttig, Neustadt (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 439 days.

(21) Appl. No.: 16/041,476

(22) Filed: Jul. 20, 2018

(65) Prior Publication Data

US 2018/0325428 A1 Nov. 15, 2018

Related U.S. Application Data

(63) Continuation of application No. PCT/EP2017/051490, filed on Jan. 25, 2017.

(30) Foreign Application Priority Data

Jan. 25, 2016 (EP) .................................. 16152623

(51) Int. Cl.
*A61B 5/1473* (2006.01)
*A61B 5/00* (2006.01)
(Continued)

(52) U.S. Cl.
CPC ........ *A61B 5/1473* (2013.01); *A61B 5/14503* (2013.01); *A61B 5/14546* (2013.01);
(Continued)

(58) Field of Classification Search
CPC .......... A61B 5/14503; A61B 2560/063; A61B 5/150282; A61B 5/150396; A61B 5/150427; A61B 5/150511
See application file for complete search history.

(56) References Cited

U.S. PATENT DOCUMENTS 5,586,553 A 12/1996 Halili et al.
5,894,373 A 4/1999 Wong
(Continued)

FOREIGN PATENT DOCUMENTS

CN 1454103 A 11/2003
CN 101574554 A 11/2009
(Continued)

OTHER PUBLICATIONS

Partial European Search Report, EP 16152623.1, dated Apr. 29, 2016, 8 pages.
(Continued)

*Primary Examiner* — Christian Jang
*Assistant Examiner* — Karen E Toth
(74) *Attorney, Agent, or Firm* — Bose McKinney & Evans LLP

(57) ABSTRACT

This disclosure concerns a medical device and a method for its production, wherein the device comprises a cannula having an elongated hollow shaft and a sharp tip provided at a distal end of the shaft, wherein the shaft is formed as a bent part from a sheet material and confines an interior passage which has a lateral slit opening, and wherein the shaft has at least one longitudinal pre-bending channel provided in the sheet material, wherein the thickness of the sheet material is reduced along the pre-bending channel and a sidewall of the shaft is folded over the pre-bending channel.

13 Claims, 3 Drawing Sheets

(51) Int. Cl.
*A61B 17/34* (2006.01)
*A61M 5/158* (2006.01)
*C12Q 1/00* (2006.01)
*G01N 27/327* (2006.01)
*A61B 5/145* (2006.01)

(52) U.S. Cl.
CPC ........ *A61B 5/6848* (2013.01); *A61B 17/3421* (2013.01); *A61B 17/3468* (2013.01); *A61M 5/158* (2013.01); *C12Q 1/001* (2013.01); *G01N 27/327* (2013.01); *A61B 5/14532* (2013.01); *A61B 2562/0295* (2013.01); *A61B 2562/125* (2013.01)

(56) References Cited

U.S. PATENT DOCUMENTS

| | | | |
|---|---|---|---|
| 6,360,888 | B1 | 3/2002 | McIvor et al. |
| 7,070,583 | B1 | 7/2006 | Higuchi et al. |
| 2007/0060814 | A1* | 3/2007 | Stafford ............... A61B 5/0002 600/365 |
| 2008/0009692 | A1 | 1/2008 | Stafford |
| 2008/0242962 | A1 | 10/2008 | Roesicke et al. |
| 2009/0112180 | A1 | 4/2009 | Krulevitch et al. |
| 2009/0156920 | A1 | 6/2009 | Kotzan et al. |
| 2009/0198202 | A1* | 8/2009 | Nedestam ............... G01N 27/72 604/361 |
| 2011/0021889 | A1 | 1/2011 | Hoss et al. |
| 2011/0224701 | A1 | 9/2011 | Menn |
| 2012/0184835 | A1 | 7/2012 | Kube et al. |
| 2012/0197222 | A1* | 8/2012 | Donnay ............. A61B 5/15107 604/318 |
| 2013/0313130 | A1 | 11/2013 | Little et al. |
| 2014/0277037 | A1* | 9/2014 | Grace .............. A61B 17/32053 606/170 |
| 2016/0008028 | A9 | 1/2016 | Matsumoto et al. |

FOREIGN PATENT DOCUMENTS

| | | |
|---|---|---|
| EP | 0 987 982 B1 | 1/2007 |
| EP | 2 713 879 A2 | 4/2014 |
| WO | WO 91/07139 A1 | 5/1991 |
| WO | WO 03/080169 A1 | 10/2003 |
| WO | WO 2007/071562 A1 | 6/2007 |
| WO | WO 2007/142561 A1 | 12/2007 |
| WO | WO 2012/089505 A1 | 7/2012 |
| WO | WO 2013/090215 A2 | 6/2013 |
| WO | WO 2013/136968 A1 | 9/2013 |

OTHER PUBLICATIONS

International Preliminary Report on Patentability, PCT/EP2017/051490, dated May 4, 2018, 17 pages.
International Search Report and Written Opinion of the International Searching Authority, PCT/EP2017/051490, dated Mar. 13, 2017, 15 pages.

* cited by examiner

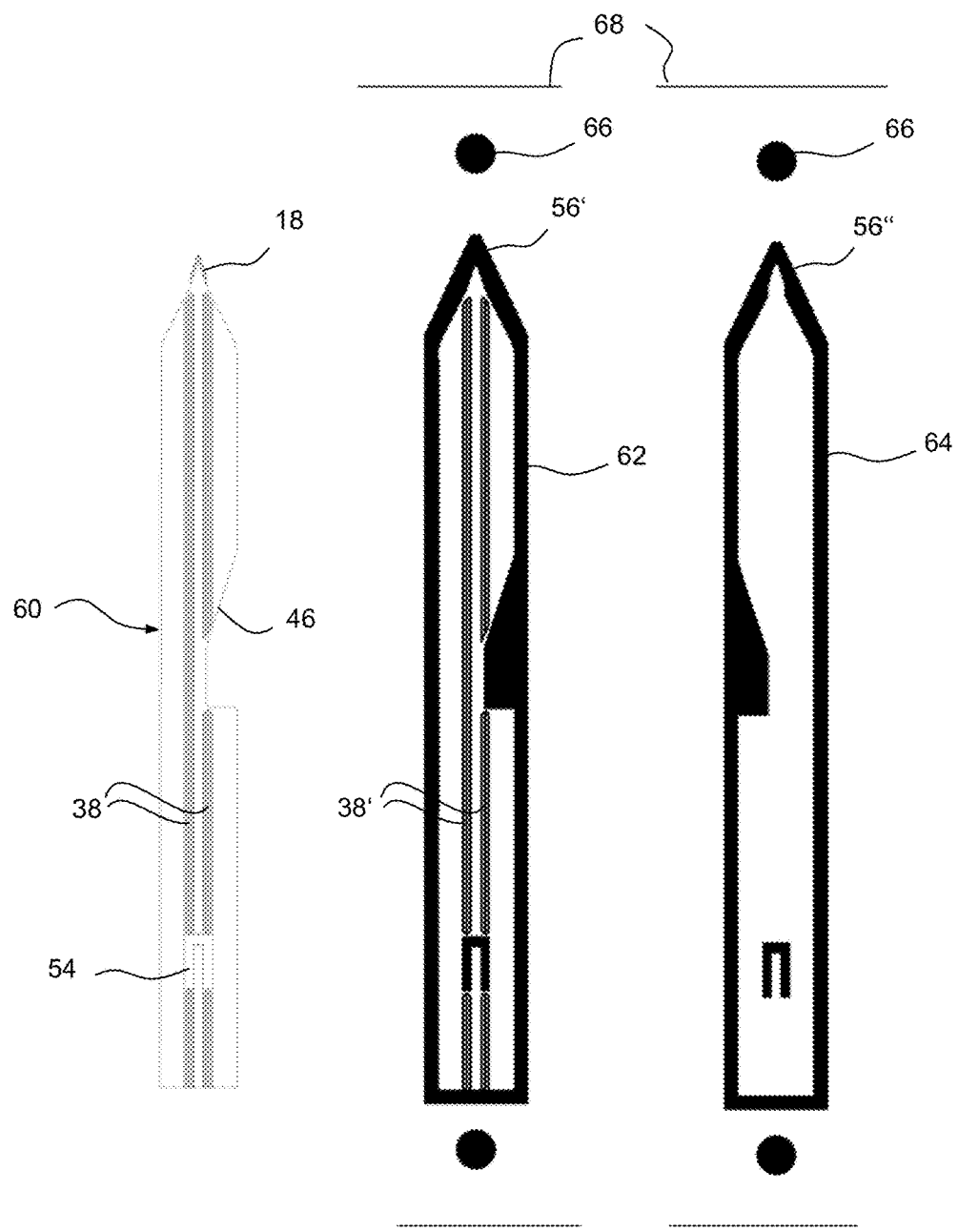
Fig.6   Fig.7   Fig.8
Fig.9

MEDICAL DEVICE AND PROCESS FOR MANUFACTURING

RELATED APPLICATIONS

This application is a continuation of PCT/EP2017/051490, filed Jan. 25, 2017, which claims priority to EP 16 152 623.1, filed Jan. 25, 2016, both of which are incorporated herein by reference in their entirety.

BACKGROUND

This disclosure concerns a medical device, in particular for insertion or implanting of a sensor or an infusion set into the skin or subcutaneous tissue of a human or mammal, comprising a cannula having an elongated hollow shaft and a sharp tip provided at a distal end of the shaft, wherein the shaft is formed as a bent part from a sheet material and confines an interior passage which has a lateral slit opening. This disclosure further concerns a method for manufacturing of such a device.

The document U.S. Publication No. 2012/0184835 discloses a sensor arrangement including a cannula that can be used to insert the sensor electrodes into the body of a patient for transcutaneous measurement. The cannula has a slit that extends along its longitudinal direction and in which the sensor shaft is arranged to be upright. The sensor head including the contact field is offset by an acute angle with respect to the sensor shaft. This is achieved by an angled layout of a substrate, which is however more difficult to produce.

SUMMARY

This disclosure improves the known devices and production methods and teaches a design which allows cost-effective manufacture and simplified system integration and use while reducing injuries upon insertion.

A first aspect of this disclosure is based on the idea of forming a hollow cannula from flat material including etched structures. Thus, it is proposed according to this disclosure that the shaft has at least one longitudinal pre-bending channel provided in the sheet material, wherein the thickness of the sheet material is reduced along the pre-bending channel and a sidewall of the shaft is folded (angled by lengthwise bending) over the pre-bending channel. The pre-bending channel(s) which define bending lines reduce the necessary bending forces and increase the tool life in the manufacturing process. Furthermore, the bending easily allows production of a slotted shaft, while maintaining a flat distal tip. Thereby it is possible to produce miniaturized parts in very high volumes in a cost efficient manner.

Advantageously, the shaft has one of a V-shaped profile along a single pre-bending channel or a trapezoidal- or square- or U-shaped profile along two parallel pre-bending channels. In this way, a concave interior is easily created to simplify mounting of a sensor.

According to a preferred implementation, the at least one pre-bending channel is formed as an etched channel in the sheet material. It is also conceivable that the pre-bending channel(s) is/are formed by punching (die-cutting) or by laser-engraving.

Preferably, the at least one pre-bending channel is arranged on the inside (inner side) of the hollow shaft such that smooth outer contours are achieved. In case of more narrow cannulas, it is also conceivable that the pre-bending channel is arranged on the outside.

It is also preferred that the sidewall of the shaft includes a bend angle through which the sheet material is bent having an apex in the pre-bending channel, and wherein the bend angle is in the range of 60° to 120°.

Another aspect of this disclosure is directed to a cutout in a folded sidewall of the shaft, wherein the cutout adjoins the slit opening and provides a side-outlet of the interior passage. In this way, it is possible to guide a generally straight bendable sensor in a proximal section of the shaft without the need of an angled sensor layout.

According to another preferred implementation, the distal side of the cutout is bordered by a transverse edge of the sidewall which is inclined towards the distal end of the shaft. Thereby, a start-up slope is created which facilitates a sensor removal out of the cannula.

Another improvement provides that a catch is formed at the outside of the shaft for fixation of the cannula on a carriage. This improves efficiency of assembly and simplifies system integration.

For further manufacturing improvement it is advantageous when the catch is a deflected segment of the sheet material of the shaft and the segment is formed by a transection of the sheet material preferably made by etching.

A particular embodiment further provides that the cutting edges are formed as a sloped blade by under-etching the sheet material, such that the sloped blade is laterally protruding over an adjacent edge section of the shaft. These measures benefit a sharp tip design while reducing skin damage during insertion.

Another improvement in this direction is achieved when the tip is a flat shaped part of the sheet material bounded by tapered cutting edges.

Preferably the at least one pre-bending channel has a distal section which ends in a distance proximal of the tip being formed as a flat shaped part, such that unwanted through-etching is avoided and the tip remains unaffected by the bending of the shaft.

Another aspect of this disclosure concerns a system including an electrochemical sensor having electrodes and conducting paths, wherein at least a proximal section of the sensor is provided in the interior passage for insertion into the skin.

For further design improvement it is advantageous when the sensor comprises a flexible linear sensor substrate which in the mounted state is angled by flexible bending and is guided out of the interior passage through the cutout in the folded sidewall of the shaft. In this way, it is possible to use a simple linear strip sensor without a complicated sensor layout.

Still another aspect of this disclosure concerns an inserter system further comprising a carriage for manipulation of the cannula by means of an inserter, wherein a proximal part of the cannula is snap-locked in the carriage.

In this connection it is further advantageous when the carriage has a back tapered recess and the shaft has a protruding catch which engages the recess.

This disclosure further concerns a process for manufacturing a medical device, comprising pre-forming a sheet material to provide a proximal shaft part and a distal tip part, forming preferably by chemical etching at least one pre-bending channel having a reduced material thickness along the shaft part, and folding the shaft part over the pre-bending channel to form an angled sidewall of a shaft which confines a concave interior passage.

In this connection, it is also advantageous when pre-forming of the sheet material and forming of the channel is achieved in one step by chemical etching.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 6 is a flat preform of the cannula photo-etched from sheet metal;

FIGS. 7 and 8 are plan views of a photomask image for the top and bottom surface of the photo-etched preform shown in FIG. 6; and FIG. 9 is a view of the proximal end face of the preform shown in FIG. 6.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
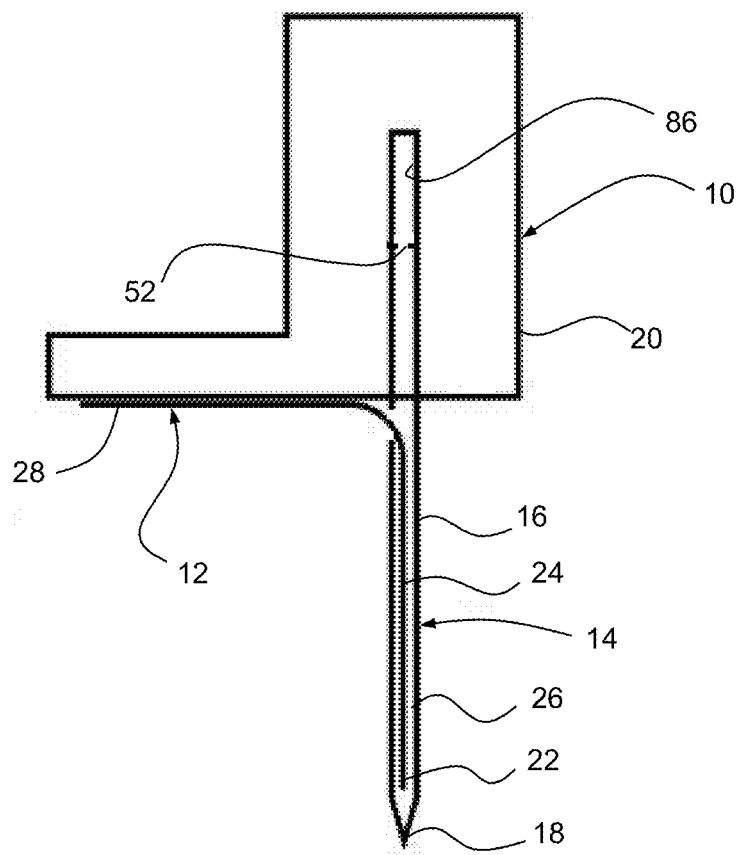
FIG. 1 is a side view of a medical device including a folded cannula for sensor implantation into skin.

FIG. 1 shows a medical device 10 provided for insertion of a sensor 12 into the skin of a human or mammal to continuously measure an analyte in bodily fluid, e.g., glucose in blood. The device 10 comprises a cannula 14 having an elongated folded shaft 16 and a tip 18 provided at the distal (free) end of the shaft 16. The shaft 16 is firmly connected to a carriage 20 of an inserter which allows an automatically driven reciprocating movement for sensor implantation. Thereby, the free sensor end 22 is placed in the puncture, while the sensor shaft 24 laterally leaves the cannula 14 during retraction through a longitudinal slit 26 in the folded shaft 16.

Figure 2:
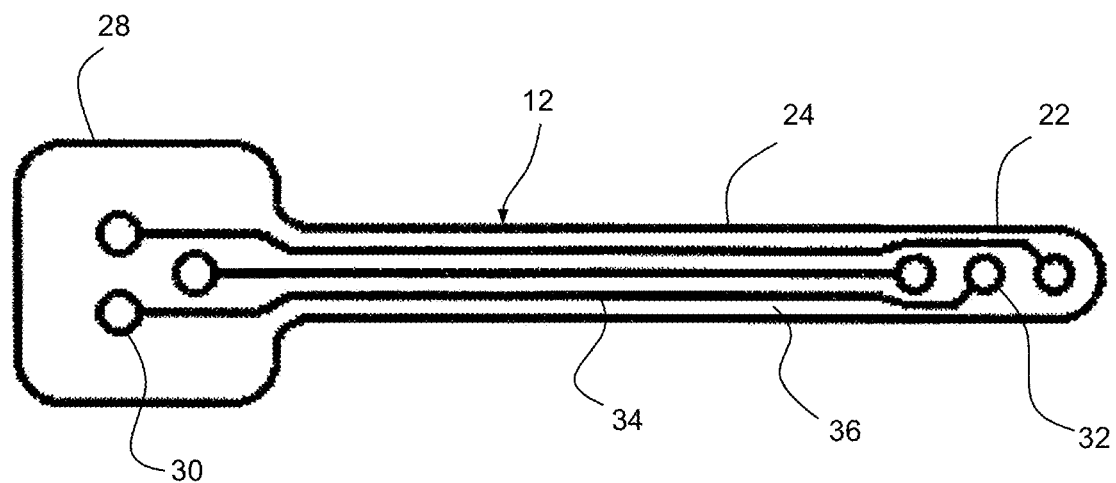
FIG. 2 is a top view of a skin-insertable electrochemical sensor.

As shown in more detail in FIG. 2, the sensor 12 has a head 28 which bears contact fields 30 to be connected to a measuring unit (not shown). For a transcutaneous measurement by electrochemical means, the free sensor end 22 carries electrodes 32 which are connected to the contact fields 20 by means of conducting paths 34. At least the sensor shaft 24 is formed from a flat substrate 36 as a straight strip. In the mounted state the flexible substrate 36 is angled by flexible bending such that the narrow side appears curved by 90° as shown in FIG. 1.

Figure 3:
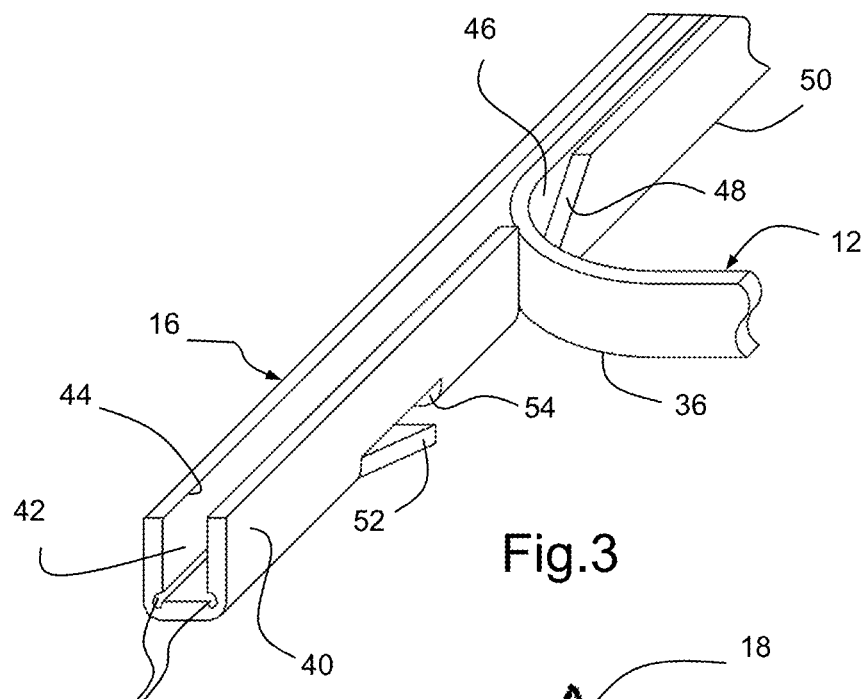
FIG. 3 is a partial perspective view of a proximal portion of the cannula and the sensor received therein.

FIG. 3 shows the configuration of the folded shaft 16 of the cannula 14 including the sensor 12. The shaft 16 has a square-shaped profile along two parallel pre-bending channels 38 which serve as bending lines for forming the shaft as a bent component from sheet metal, as will be explained in more detail below. Thereby, the sidewall 40 of the shaft 16 is angled over the pre-bending channels 38 to assume a U-shaped configuration which confines an interior passage 42 having a lateral slit opening 44 along its length. Generally, the bend angle may be less or larger than 90° and may vary in different sections of the shaft 16. In case of a relatively wide interior passage 42, it is preferred that the pre-bending channels 38 are arranged on the inner side of the shaft 16.

As is further apparent from FIG. 3, a cutout 46 is provided in an upstanding flank of the folded sidewall 40 for guiding the bent substrate 36 of the sensor 12. The cutout 46 adjoins the slit opening 44 at the edge of the sidewall 40 and tapers to the base of the U-Profile in a generally trapezoid-like shape. Preferably, the clearance at the base is at least adapted to the thickness of the sensor substrate 36. The height of the cutout 46 may be equal to the height of the upstanding flank or may be less in order to improve bending stiffness of the shaft 16.

The combination of the slit opening 44 and the cutout 46 allows mounting the sensor 12 by a lateral insertion movement of a few millimeters. In contrast, conventional designs of slotted needles require an infeed from the distal end over the whole needle length.

In order to support a self-acting pull out of the sensor 12 out of the interior passage 42 during retraction of the cannula 14, the distal side of the cutout 46 is bordered by a sloped transverse edge 48 which is inclined towards the distal end of the shaft 16 (i.e., inclined in the direction toward the tip) and thereby forms a start-up slope. The slope angle as included between the edge transverse 48 and the base edge 50 lies in the range of 3° to 45°, preferably 8° to 30° and most preferred 18° to 22°.

For simplification of assembly, the shaft 16 is provided with a catch 52 protruding at the outside and allowing a snap-lock in the carriage 20. The catch 52 is provided as a deflected base segment of the shaft 16 which is produced by a transection 54 of the sheet material. It is also conceivable to create the catch by the upstanding proximal section of the sidewall 40 bordering the cutout 46 and having a reduced bend angle as compared to a distal section. To allow simple connection assembly, the carriage 20 has a back tapered recess or plugin channel 86 (FIG. 1), wherein the catch 52 engages inseparably.

Figure 4:
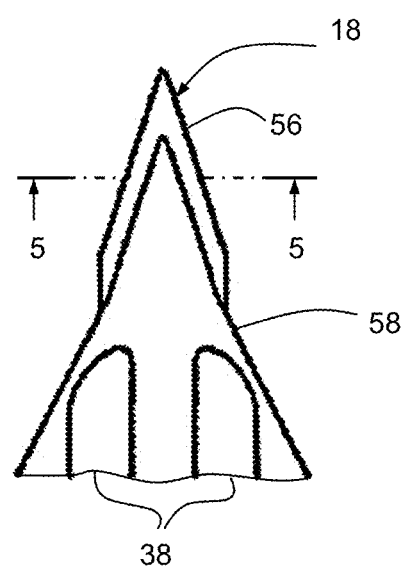
FIG. 4 is a plan view of the tip of the cannula.

FIG. 4 shows the tip 18 which has a generally flat configuration shaped by, e.g., photo-chemical etching. The tip 18 remains unaffected by the metal working or bending of the shaft 16. Thus, the pre-bending channels 38 end at a distance proximal of the tip 18. Advantageously, the sharp tip 18 in top-view includes an angle of 30° to 40° and an apex radius of preferred 5 to 30 μm.

Figure 5:
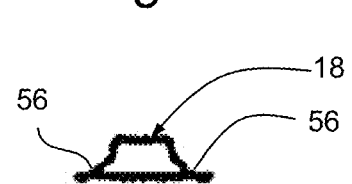
FIG. 5 is a cross-sectional view of the tip along the line 5-5 in FIG. 4.

The tip 18 is defined by tapered cutting edges 56 which are laterally protruding over a proximally adjacent edge section 58. As illustrated in the sectional view of FIG. 5, the cutting edges 56 are formed as a blade sloped to one side of the sheet metal—in the case shown to the bottom side. This can be achieved by lateral under-etching of the sheet material, as explained below. In tests carried out with artificial skin, it has been found that such a tip geometry significantly reduces skin damage as compared to an integrated blade which does not protrude over the edge section 58.

FIG. 6 shows a flat preform 60 of the cannula as produced by photo-etching (also referred to as chemical milling or photo chemical machining) from sheet metal in a cost efficient way. This method allows a high degree of freedom in the layout design without the need for additional cutting work. The flat preform 60 includes the tip 18 and the section of the shaft 16 provided with the pre-bending channels 38, the cutout 46 and the U-shaped transection 54 for producing the catch 52.

All these elements can be shaped by photomask images for the top and bottom surface of the sheet metal as shown in FIGS. 7 and 8. The respective photomasks 62, 64 are not exact mirror images, but differ in the channel forming portions 38' for the channels 38 and the blade forming portions 56', 56" for the blades 56 of the tip 18. The masks 62, 64 are positioned above each other by means of index points 66 as to make them in perfect alignment.

The sheet metal is preferably medical-grade stainless steel with a thickness in the range of 80 to 200 μm, preferably 100 to 130 μm.

An etching agent to the sheet metal is subsequently applied over the double-sided mask generated in this manner so that the masked areas are etched away according to the desired basic shape. In the case of an isotropic etching action, the depth of the removed material corresponds to the lateral etching rate for the undercutting of edge contours. The etching process can also take place anisotropically due to external influencing parameters or material properties of the substrate, i.e., the lateral undercutting rate is then larger or smaller than the depth etching rate. The etching allows separating of workpieces in very large numbers from a ribbon-like sheet material 68 without need for additional tools and handling/machining of individual parts. Usually in uncritical positions at least one junction between a workpiece and a ribbon-like sheet holds the workpiece in place. This junction, which is not shown, may be provided with an etched predetermined breaking line to allow the final separation of individual parts even without tools just by breaking, for instance by bending the individual part along the breaking line.

FIG. 9 shows the pre-bending channels 38 produced by chemical etching in the flat preform 60. The width of the channels is larger than the depth. The depth should be designed such that the material is sufficiently weakened for simplified bending, but remains still sufficiently thick to guarantee an adequate stiffness of the bent cannula. The pre-bending channels 38 are terminated before the tip area, in order to avoid unwanted through-etching which would lead to increased injuries in the skin puncture.

The process of chemical etching or milling leads to sharp edges, specifically in along the blades 56 which may lead to increased skin tearing. Such unwanted effects can be avoided by rounding the edges by means of electrochemical polishing. In this process step, the preform 60 is immersed in a bath of electrolyte and serves as the anode. A current passes from the anode, where metal on the surface is oxidized and dissolved in the electrolyte. Thereby, the protruding parts of an edge profile dissolve faster than the recesses. It is also possible to partly mask or cover areas like the sharp tip which should not be further rounded.

When conducting pricking tests in artificial skin, it could be demonstrated that electro-polishing leads to enhanced surface properties and reduces the punctures grooves to an area which is up to 5 times smaller in comparison to untreated workpieces. Apparently, the tip 18 opens the skin, while the blunt electro-polished blades 56 aid to displace the tissue without additional trauma.

Thereafter, the cannula 14 is finished by bending the preform 60 in a suitable tool. This can be achieved by a die block which presses the sheet material to form the U-shape as shown in FIG. 3. The residual stress may cause the material to spring back, so the sheet must be over-bent to achieve the proper bend angle. If the width of the slit opening 44 is larger than the base width, the insertion of the sensor is simplified, though the overall cross section is increased. In any case, the pre-bending channels 38 reduce the necessary bending forces and protect the necessary bending tooling from early wear.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A cannula for subcutaneous insertion of a sensor or an infusion set, comprising:
    an elongated hollow shaft formed from bent sheet material and defining an interior passage which has a lateral slit opening extending along a longitudinal direction of the shaft;
    the shaft having at least one longitudinal pre-bending channel in the sheet material, wherein the thickness of the sheet material is reduced along the at least one pre-bending channel, and a sidewall of the shaft is folded over the at least one pre-bending channel; and
    a sharp tip provided at a distal end of the shaft, wherein the tip comprises a flat part of the sheet material bounded by straight cutting edges, each cutting edge being tapered, wherein the cutting edges laterally protrude distally beyond the edge section beginning in an area surrounding the tip and terminating in an area distal of the at least one pre-bending channel.

2. The cannula according to claim 1, wherein the shaft has one of the following profiles:
    a V-shaped profile along a single pre-bending channel;
    (ii) a trapezoidal-shaped profile along two parallel pre-bending channels;
    (iii) a square-shaped profile along two parallel pre-bending channels.

3. The cannula according to claim 1, wherein the at least one pre-bending channel is etched in the sheet material.

4. The cannula according to claim 1, wherein the sidewall includes a bend angle through which the sheet material is bent having an apex in the pre-bending channel, wherein the bend angle is from 60° to 120°.

5. The cannula according to claim 1, wherein the cutting edges are blades that are sloped to one side of the sheet material.

6. The cannula of claim 1, wherein the cutting edges are rounded by etching.

7. The cannula according to claim 1, further comprising a cutout in the folded sidewall of the shaft, the cutout adjoining the slit opening and providing a side-outlet of the interior passage, wherein the cutout is configured to guide a sensor out of the interior passage.

8. The cannula according to claim 1, wherein the at least one pre-bending channel has a distal section which ends at a location spaced from the tip.

9. The cannula assembly of claim 8, wherein the edges of the tip in the longitudinal direction away from the apex of the tip form an angle with a longitudinal axis of the shaft of between 30° to 40°.

10. The cannula assembly of claim 8, wherein the tip has an apex radius of between 5 to 30 μm.

11. The cannula according to claim 1, further comprising a catch configured to fix the cannula to a carriage.

12. The cannula according to claim 1, further comprising an electrochemical sensor having electrodes and conducting paths, wherein at least a proximal section of the sensor is provided in the interior passage for insertion into the skin.

13. A cannula for subcutaneous insertion of a sensor or an infusion set, comprising:
- an elongated hollow shaft formed from bent sheet material and defining an interior passage which has a lateral slit opening extending along a longitudinal direction of the shaft;
- the shaft having at least one longitudinal pre-bending channel in the sheet material, wherein the thickness of the sheet material is reduced along the at least one pre-bending channel, and a sidewall of the shaft is folded over the at least one pre-bending channel;
- a sharp tip provided at a distal end of the shaft, wherein the tip comprises a flat part of the sheet material bounded by cutting edges, each cutting edge being tapered, wherein the cutting edges laterally protrude distally beyond the edge section beginning in an area surrounding the tip and terminating in an area distal of the at least one pre-bending channel; and
- a cutout in the folded sidewall of the shaft;
- wherein, the at least one pre-bending channel has a distal section which ends at a location spaced from the tip.

\* \* \* \* \*